United States Patent
Mu et al.

(10) Patent No.: US 10,351,888 B2
(45) Date of Patent: Jul. 16, 2019

(54) HIGHLY EFFICIENT METHOD FOR SYNTHESIZING DIFRUCTOSE ANHYDRIDE III

(71) Applicant: Jiangnan University, Wuxi (CN)

(72) Inventors: Wanmeng Mu, Wuxi (CN); Bo Jiang, Wuxi (CN); Shuhuai Yu, Wuxi (CN); Yingying Zhu, Wuxi (CN); Tao Zhang, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 15/777,932

(22) PCT Filed: Apr. 15, 2016

(86) PCT No.: PCT/CN2016/079428
§ 371 (c)(1),
(2) Date: May 22, 2018

(87) PCT Pub. No.: WO2017/128529
PCT Pub. Date: Aug. 3, 2017

(65) Prior Publication Data
US 2019/0002939 A1 Jan. 3, 2019

(30) Foreign Application Priority Data
Jan. 26, 2016 (CN) .......................... 2016 1 0053213

(51) Int. Cl.
| | |
|---|---|
| *C12P 19/12* | (2006.01) |
| *C12P 19/18* | (2006.01) |
| *C12P 19/14* | (2006.01) |
| *C12N 9/10* | (2006.01) |
| *C12N 9/88* | (2006.01) |

(52) U.S. Cl.
CPC ............ *C12P 19/12* (2013.01); *C12N 9/1051* (2013.01); *C12N 9/88* (2013.01); *C12P 19/14* (2013.01); *C12P 19/18* (2013.01); *C12Y 204/01009* (2013.01); *C12Y 402/02017* (2013.01); *C12Y 402/02018* (2013.01)

(58) Field of Classification Search
None
See application file for complete search history.

(56) References Cited

FOREIGN PATENT DOCUMENTS

| | | |
|---|---|---|
| CN | 101090906 A | 12/2007 |
| CN | 101906405 A | 12/2010 |
| CN | 101974584 A | 2/2011 |
| CN | 104087604 A | 10/2014 |
| CN | 104097537 A | 10/2014 |
| EP | 1834957 | * 12/2004 |

OTHER PUBLICATIONS

Machine translation of CN101974584, translated by https://worldwide.espacenet.com/ on Jan. 10, 2019 (Year: 2019).*
M.A. Anwar et al. "Inulin and levan synthesis by probiotic Lactobacillus gasseri strains: characterization of three novelfructansucrase enzymes and their fructan products", Microbiology 156:1264-1274. (Year: 2010).*
Genbank, accession No. WP_018778058.1, Jun. 29, 2013 (Jun. 29, 2013), [retrieve date: Oct. 24, 2016 (Oct. 24, 2016) ], retrieved from NCBI.

* cited by examiner

*Primary Examiner* — Rebecca E Prouty
(74) *Attorney, Agent, or Firm* — IPro, PLLC; Na Xu

(57) ABSTRACT

The invention discloses a high-efficiency synthesis method of difructose anhydride III. The method comprises the following steps: firstly converting sucrose into inulin by using inulosucrase without separating polysaccharide, and then converting inulin by using inulin fructotransferase to synthesize the functional disaccharide difructose anhydride III. The method has the advantages of simple process and high efficiency, and a conversion rate of synthesizing inulin into difructose anhydride III can reach 40%-54%. In order to obtain purer difructose anhydride III, yeast is utilized to remove small molecule monosaccharides in a reaction solution, and the finally obtained purer difructose anhydride III can be easily separated and purified. Thus, the method has broad market application prospects.

7 Claims, 2 Drawing Sheets
Specification includes a Sequence Listing.

HIGHLY EFFICIENT METHOD FOR SYNTHESIZING DIFRUCTOSE ANHYDRIDE III

TECHNICAL FIELD

The disclosure herein relates to the field of a high-efficiency synthesis method of difructose anhydride III, particularly a two-enzyme two-step method for implementing high-efficiency production of difructose anhydride III (DFA III), belonging to the technical field of bioprocessing of functional food.

BACKGROUND

In recent years, because of the improvement of living standard, diabetes, obesity and cardiovascular diseases increase by years, and a younger-age trend occurs. Therefore, the development of a lower-energy multifunctional sweetener with nutritional properties is becoming a focal issue of consumers.

Difructose anhydride III is a novel functional sweetener, of which the structure is mainly formed by removing two water molecules from two fructose molecules. Since all hydroxyl groups in anomeric carbon become glycosidic bonds, the difructose anhydride III is a novel non-reducing disaccharide. Because of the existence of such a special form of diglycosidic bonds, the difructose anhydride III has very stable properties. The difructose anhydride III is quite stable for heat and acids, can resist high temperature, and cannot generate the phenomenon of browning or decomposition during high-temperature processing of common food. The sweetness of the difructose anhydride III is only ½ that of sucrose, but the heat is lower than that of sucrose, and is only 1/15 that of sucrose (0.263 kcal/g), so the difructose anhydride III has good functions for patients with diabetes and obesity; and therefore, the difructose anhydride III can be used as an ideal sucrose substitute in low-energy food and diabetic food for preventing and treating diabetes. In the meanwhile, the difructose anhydride III has lower hydroscopicity than the sucrose, and does not absorb moisture under the relative humidity of 74%, thereby facilitating the storage of sugar. The difructose anhydride III cannot be absorbed by the intestinal tract, thus cannot generate energy, and therefore, can be used as a sweetener for adjuvant therapy of weight loss. Although the difructose anhydride III cannot be directly digested and absorbed by the intestinal tract of the human body, the difructose anhydride III can be utilized and metabolized by probiotics in the intestinal tract to generate abundant prebiotics, thereby promoting growth of probiotics in the human body and good health of the human body. The difructose anhydride III can promote the absorption of calcium, magnesium, zinc, copper and other mineral elements as well as flavonoids by the human body, and thus, has the effects of promoting bone growth, etc. Dental caries is mainly caused by corrosion of teeth due to acids produced by sucrose and other saccharides as *streptococcus mutans* metabolize in a cavity. However, the difructose anhydride cannot be metabolized by the *streptococcus mutans*, and thus, has the effect of inhibiting dental caries. Besides, the difructose anhydride III has multiple physiological functions of lowering cholesterol, high blood pressure and the like. In view of the favorable properties of the difructose anhydride III, the difructose anhydride III can be used as a food additive in bakery food, beverages, candies, etc. Therefore, the difructose anhydride III has broad prospects in food industry.

The difructose anhydride exists in the natural world, mainly in compositae, such as *cichorium intybus*, Jerusalem artichoke, etc., but is lower in content. Besides, a small amount of difructose anhydride III also exists in processing of honey, coffee, etc. The content of the difructose anhydride III is lower in the natural world, so the cost for extracting and separating difructose anhydride III is very high. Although the difructose anhydride III can be produced by chemical methods, the chemical synthesis methods have many adverse factors, such as environmental pollution, etc. The difructose anhydride can also be obtained by a biological catalysis method. In 1973, Uchiyama T detected inulin fructotransferase (EC 4.2.2.18) in *Arthrobacter ureafaciens* for the first time, and after that, it has been detected that a dozen of microorganisms can generate inulin fructotransferase. The bioconversion method has the advantages of wide raw material sources, low price, high conversion rate and suitability for industrial production. However, in all existing methods, the difructose anhydride III is obtained by directly converting plant inulin, which firstly requires plant inulin; and inulin has higher price than sucrose, so the existing methods are not economically efficient.

The inventor provides a method using cheaper sucrose as a substrate: the sucrose is firstly converted into inulin by inulosucrase, and the synthesized biological inulin is directly converted into difructose anhydride III by inulin fructotransferase; and in this process, the separation and purification of the inulin are not required, thereby reducing the energy consumption and lowering production cost; and finally, other saccharides existing in a reaction solution are removed by yeast to obtain the purer difructose anhydride III, thereby facilitating the subsequent separation and purification.

SUMMARY

The invention aims to provide a cheap high-efficiency synthesis method of difructose anhydride III. The difructose anhydride III prepared by the method has higher purity. The whole synthesis process has the advantages of simple technique, high efficiency and low cost.

The technical scheme of the invention is as follows:

High-efficiency synthesis steps of difructose anhydride III comprise:

1) firstly converting sucrose into inulin by using inulosucrase without separating polysaccharide; and 2) then converting the inulin by using inulin fructotransferase to synthesize the functional disaccharide difructose anhydride III.

A process for converting sucrose into inulin comprises: completely dissolving the sucrose in water, controlling concentration to be 300-500 g/l, regulating a pH value to be 5.0-6.0, controlling temperature to be 20-30° C., adding inulosucrase (addition amount being 1-15 U/g), and performing thermostatic reaction for 25-60 minutes.

In order to get better effects, the preferable process is that the process for converting sucrose into inulin is preferably as follows: the addition amount of the inulosucrase is controlled to be 5-15 U/g, the pH is controlled to be 5.0-6.0, the temperature is controlled to be 20-30 DEG C., and the thermostatic reaction lasts for 30-60 minutes.

The process for converting inulin into difructose anhydride III comprises: heating a sucrose conversion solution to 50-60° C., adding inulin fructotransferase (the concentration of the added inulin fructotransferase being 1-20 U/g) into the sucrose conversion solution, controlling the pH value to be still 5.0-6.0, and performing thermostatic reaction for 2-20 hours.

In order to get better effects, the preferable process is characterized in that the process for converting inulin into difructose anhydride III is preferably as follows: the concentration of the inulin fructotransferase is 5-10 U/g, the pH value is controlled at 5.0-6.0, the temperature is controlled at 55-60° C., and the thermostatic reaction lasts for 6-12 hours.

In order to further lower the cost, a step of eliminating residual saccharides from the conversion solution can also be added to remove sucrose, glucose, fructose and part of fructooligosaccharides therein, wherein the addition of yeast and other modes are utilized to remove the residual saccharides.

When the yeast is used for removing the residual saccharides, a concrete scheme is as follows: cool a reaction solution, add the yeast to absorb and remove sucrose, glucose, fructose and part of fructooligosaccharides in the reaction solution, control pH to be 5.0-6.0, control the temperature to be 28° C., and react in a 200 rpm shaking table for 24-36 hours.

An amino acid sequence of the inulosucrase is as shown in SEQ ID NO.1.

An amino acid sequence of the inulin fructotransferase is as shown in SEQ ID NO.2.

A method for detecting difructose anhydride III comprises:

Filtering supernate after reaction by a microporous filter membrane (0.22), and analyzing the filtrate by HPLC equipped with a differential refraction display. HPLC conditions are as follows: a Sugarpak1, 6.5 mm id×300 mm calcium cation exchange column is used, pure water is used as a mobile phase, column temperature is 85° C., flow velocity is 0.4 ml/min, and sample size is 10 μl. The concentration of a difructose anhydride III standard sample is 0.5%. The concentration of the difructose anhydride III synthesized in the reaction solution is calculated by utilizing a ratio of the peak area of the difructose anhydride III in the solution obtained by the detection (3) reaction to the peak area of the 0.5% difructose anhydride III standard sample.

The cheap substrate sucrose is firstly converted into the inulin by using the inulosucrase, and then the synthesized biological inulin is converted into the difructose anhydride III by using the inulin fructotransferase, thereby avoiding the process of separating and purifying the inulin. Since the plant inulin has higher market price than sucrose, the cost is lowered by directly converting sucrose into inulin. A conversion rate of catalyzing inulin into difructose anhydride III by the inulin fructotransferase can reach 54%. Finally, other saccharides in a reaction system are removed by using yeast to obtain the purer difructose anhydride III. The whole process is simpler, has the advantages of low production cost and low energy consumption, and is convenient for implementing industrial production.

DETAILED DESCRIPTION

Figure 1:
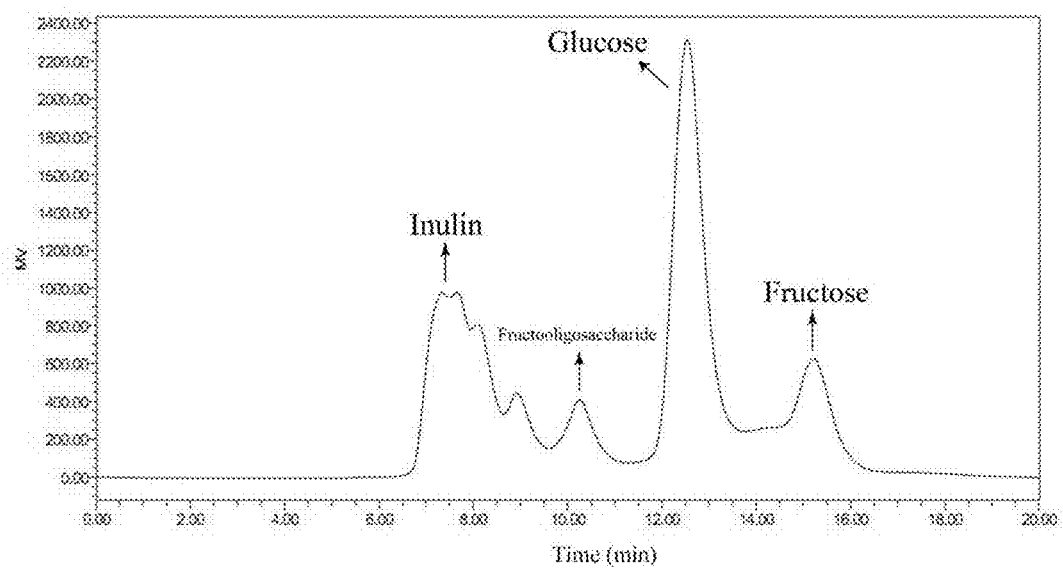
FIG. 1: Synthesis of inulin (diluted solution) from substrate sucrose by using inulosucrase.
Figure 2:
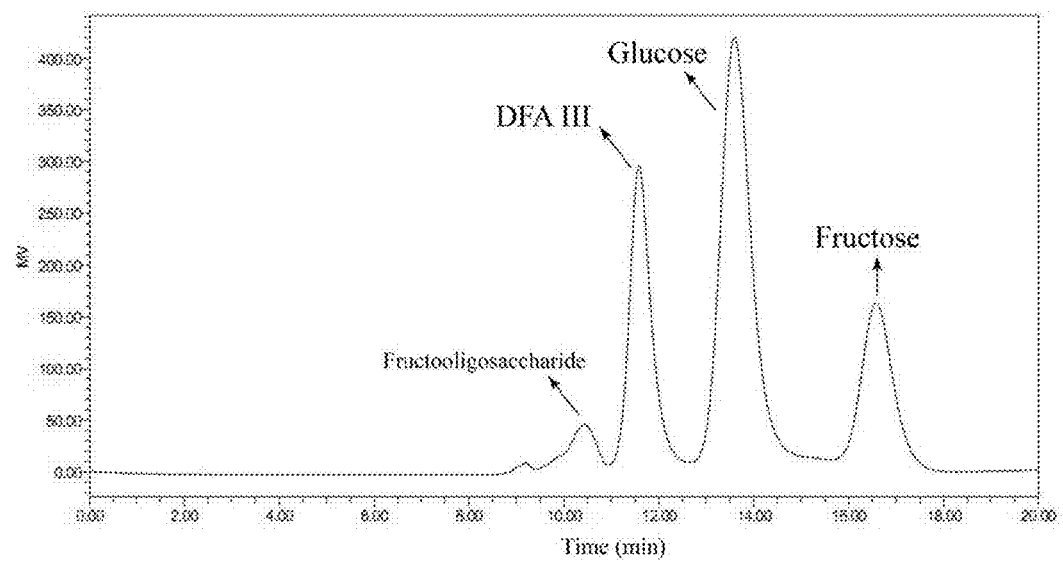
FIG. 2: Conversion of synthesized inulin into difructose anhydride III (diluted solution) by using inulin fructotransferase.
Figure 3:
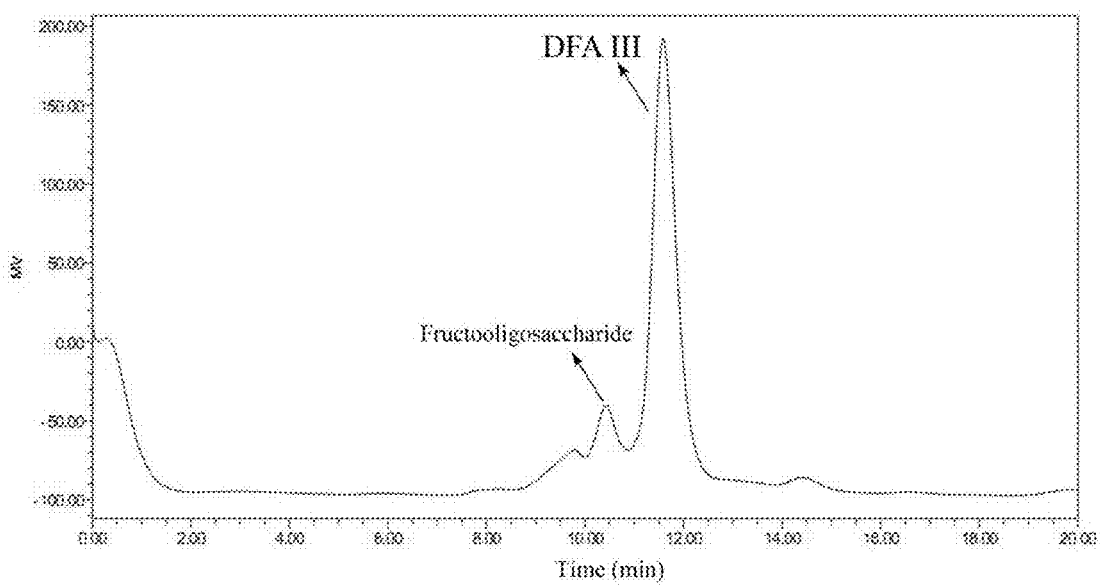
FIG. 3: Treatment of the synthesized difructose anhydride III solution by using yeast.

The examples of converting sucrose into difructose anhydride III by using inulosucrase and inulin fructotransferase are as follows. The method of the invention is illustrated by the examples, but is not limited to the examples listed.

Example 1

Completely dissolve substrate sucrose in water, control concentration to be 400 g/l, regulate a pH value to be 5.5, control temperature to be 20° C., add inulosucrase (addition amount being 10 U/g of sucrose), and perform thermostatic reaction for 30 minutes;

Increase the temperature of a reaction system to 55° C., add inulin fructotransferase into the reaction system (the concentration of the added inulin fructotransferase being 5 U/g), control the pH value to be still 5.5, and perform thermostatic reaction for 12 hours.

Take a solution after reaction, centrifuge, filter supernate through a microporous filter membrane (0.22), and analyze the filtrate by HPLC equipped with a differential refraction display. HPLC conditions are as follows: a Sugarpak1, 6.5 mm id×300 mm calcium cation exchange column is used, pure water is used as a mobile phase, column temperature is 85° C., and flow velocity is 0.4 ml/min, and the sample size is 10 μl. The concentration of a difructose anhydride III standard sample is 0.5%. The concentration of the difructose anhydride III synthesized in the reaction solution is calculated by utilizing a ratio of the peak area of the difructose anhydride III in the reaction solution to the peak area of the 0.5% difructose anhydride III standard sample. A conversion rate of the obtained difructose anhydride III is up to 54%.

Example 2

Completely dissolve substrate sucrose in water, control concentration to be 300 g/l, regulate a pH value to be 5.0, control temperature to be 22° C., add inulosucrase (addition amount being 15 U/g of sucrose), and perform thermostatic reaction for 60 minutes;

Increase the temperature of a reaction system to 60° C., adding inulin fructotransferase into the reaction system (the concentration of the added inulin fructotransferase being 10 U/g), control the pH value to be still 5.0, and perform thermostatic reaction for 6 hours. A conversion rate of the obtained difructose anhydride III is up to 48%.

Example 3

Completely dissolve substrate sucrose in water, control concentration to be 500 g/l, regulate a pH value to be 6.0, control temperature to be 30° C., adding inulosucrase (addition amount being 5 U/g of sucrose), and perform thermostatic reaction for 60 minutes;

Increase the temperature of a reaction system to 50° C., add inulin fructotransferase into the reaction system (the concentration of the added inulin fructotransferase being 20 U/g), control the pH value to be still 6.0, and perform thermostatic reaction for 20 hours. A conversion rate of the obtained difructose anhydride III is up to 43%.

Example 4

Produce difructose anhydride III according to reaction and detection conditions in Embodiment 1, naturally cool a reaction system to 28° C., add yeast into the reaction system, control pH to be 5.0-6.0. and react in a 28° C. 200 rpm shaking table for 24-36 hours. The present embodiment is mainly implemented by removing sucrose, glucose, fructose and part of fructooligosaccharides in a reaction solution by yeast fermentation to obtain the purer difructose anhydride III, thereby facilitating the subsequent detection and separation purification in industrial implementation. Finally, a conversion rate of difructose anhydride III is close to that in Embodiment 1, but the solution after reaction does not contain sucrose, glucose, fructose and part of fructooligosaccharides any more, thereby improving the purity of the difructose anhydride.

What is claimed is:
1. A method of synthesizing with high efficiency difructose anhydride III, comprising firstly converting sucrose into inulin by adding inulosucrase without separating polysaccharide, and then converting inulin by adding inulin fructotransferase to synthesize the functional disaccharide difructose anhydride III; wherein the amino acid sequence of the inulosucrase is set forth in SEQ ID NO.1; wherein the process for converting sucrose into inulin comprises: completely dissolving the sucrose in water, wherein the concentration of the sucrose is at 400-500 g/l, regulating pH to be at 5.0-6.0, controlling temperature to be at 20-30° C., adding inulosucrase with an amount of 1-15 U/g of sucrose, and performing thermostatic reaction for 25-60 minutes to obtain a sucrose conversion solution; wherein the process for converting inulin into difructose anhydride III comprises: heating the sucrose conversion solution to 50-60° C., and adding inulin fructotransferase into the sucrose conversion solution, wherein the concentration of the inulin fructotransferase is at 1-20 U/g of the sucrose conversion solution, controlling the pH to be at 5.0-6.0, and performing thermostatic reaction for 2-12 hours.

2. The method of claim 1, wherein the the inulosucrase is controlled to be at 5-15 U/g of sucrose, pH is controlled to be at 5.0-6.0, the temperature is controlled to be at 20-30 DEG C., and the thermostatic reaction lasts for 30-60 minutes.

3. The method of claim 1, wherein the concentration of the inulin fructotransferase is 5-10 U/g of the sucrose conversion solution, the pH value is controlled to be at 5.0-6.0, the temperature is controlled to be at 55-60° C., and the thermostatic reaction lasts for 6-12 hours.

4. The method of claim 1, further comprising a step of eliminating residual saccharides to remove sucrose, glucose, fructose and part of fructooligosaccharides therein.

5. The method of claim 4, further comprising removing residual saccharides by adding yeast.

6. The method of claim 1, wherein the amino acid sequence of the inulin fructotransferase is set forth in SEQ ID NO.2.

7. The method of claim 4, further comprising cooling the reaction solution, adding yeast into the reaction solution to absorb and remove the sucrose, the glucose, the fructose and part of the fructooligosaccharides in the reaction solution, controlling pH to be at 5.0-6.0, controlling temperature to be at 28° C., and reacting in a 200 rpm shaking table for 24-36 hours.

* * * * *

```
                          SEQUENCE LISTING

<160> NUMBER OF SEQ ID NOS: 2

<210> SEQ ID NO 1
<211> LENGTH: 566
<212> TYPE: PRT
<213> ORGANISM: Artificial Sequence
<220> FEATURE:
<223> OTHER INFORMATION: Protein translated from Synthetic DNA

<400> SEQUENCE: 1

Met Ala Val Lys Gln Asp Glu Lys Ala Ala Thr Ala Val Lys Ala Asn
1               5                   10                  15

Thr Glu Val Lys Ala Asn Glu Thr Ser Thr Lys Ser Ala Ser Lys Asp
            20                  25                  30

Asn Lys Ala Glu Leu Lys Gly Gln Ile Lys Asp Ile Val Lys Glu Ser
        35                  40                  45

Gly Val Asp Thr Ser Lys Leu Thr Asp Asp Gln Ile Asn Glu Leu Asn
    50                  55                  60

Lys Ile Ser Phe Ser Lys Glu Ala Lys Ser Gly Thr Gln Leu Thr Tyr
65                  70                  75                  80

Ser Asp Phe Lys Lys Ile Ala Lys Thr Leu Ile Glu Gln Asp Ala Arg
                85                  90                  95

Tyr Ala Val Pro Phe Phe Asn Ala Ser Lys Ile Lys Asn Met Pro Ala
            100                 105                 110

Ala Lys Thr Leu Asp Ala Gln Thr Gly Lys Val Glu Asp Leu Glu Ile
        115                 120                 125

Trp Asp Ser Trp Pro Val Gln Asp Ala Lys Thr Gly Tyr Val Ser Asn
    130                 135                 140

Trp Asn Gly Tyr Gln Leu Val Ile Gly Met Met Gly Val Pro Asn Thr
145                 150                 155                 160

Asn Asp Asn His Ile Tyr Leu Leu Tyr Asn Lys Tyr Gly Asp Asn Asn
                165                 170                 175

Phe Asn Asn Trp Lys Asn Ala Gly Pro Ile Phe Gly Leu Gly Thr Pro
            180                 185                 190

Val Ile Gln Gln Trp Ser Gly Ser Ala Thr Leu Asn Lys Asp Gly Ser
        195                 200                 205

Ile Gln Leu Tyr Tyr Thr Lys Val Asp Thr Ser Asp Asn Asn Thr Asn
    210                 215                 220

His Gln Lys Ile Ala Ser Ala Thr Val Tyr Leu Asn Leu Glu Lys Asn
225                 230                 235                 240

Gln Asp Lys Ile Ser Ile Ala His Val Asp Asn Asp His Ile Val Phe
                245                 250                 255

Glu Gly Asp Gly Tyr His Tyr Gln Thr Tyr Asn Gln Trp Lys Lys Thr
            260                 265                 270

Asn Lys Gly Ala Asp Asn Ile Ala Met Arg Asp Ala His Val Ile Asp
        275                 280                 285

Asp Lys Asp Gly Asn Arg Tyr Leu Val Phe Glu Ala Ser Thr Gly Thr
    290                 295                 300

Glu Asn Tyr Gln Gly Ala Asp Gln Ile Tyr Gln Trp Leu Asn Tyr Gly
```

```
                305                 310                 315                 320
Gly Thr Asn Lys Asp Asn Leu Gly Asp Phe Leu Gln Ile Leu Ser Asn
                    325                 330                 335

Ser Asp Ile Lys Asp Arg Ala Lys Trp Ser Asn Ala Ala Ile Gly Ile
                340                 345                 350

Ile Lys Leu Asn Asn Asp Thr Lys Asn Pro Gly Val Glu Lys Val Tyr
                355                 360                 365

Thr Pro Leu Ile Ser Ala Pro Met Val Ser Asp Glu Ile Glu Arg Pro
            370                 375                 380

Asp Val Val Arg Leu Gly Asn Lys Tyr Tyr Leu Phe Ala Ala Thr Arg
385                 390                 395                 400

Leu Asn Arg Gly Ser Asn Asp Ala Trp Met Ala Ala Asn Lys Ala
                    405                 410                 415

Val Gly Asp Asn Val Ala Met Ile Gly Tyr Val Ser Asn Leu Thr
                420                 425                 430

His Gly Tyr Val Pro Leu Asn Glu Ser Gly Val Val Leu Thr Ala Ser
                435                 440                 445

Val Pro Ala Asn Trp Arg Thr Ala Thr Tyr Ser Tyr Tyr Ala Val Pro
450                 455                 460

Val Glu Gly Arg Asp Asp Gln Leu Leu Ile Thr Ser Tyr Ile Thr Asn
465                 470                 475                 480

Arg Gly Glu Val Ala Gly Lys Gly Met His Ala Thr Trp Ala Pro Ser
                    485                 490                 495

Phe Leu Leu Gln Ile Asn Pro Asp Asn Thr Thr Val Leu Ala Lys
                500                 505                 510

Met Thr Asn Gln Gly Asp Trp Ile Trp Asp Asp Ser Ser Glu Asn Ala
                515                 520                 525

Asp Met Met Gly Val Leu Glu Lys Asp Ala Pro Asn Ser Ala Ala Leu
                530                 535                 540

Pro Gly Glu Trp Gly Lys Pro Val Asp Trp Asp Leu Ile Gly Gly Tyr
545                 550                 555                 560

Asn Leu Lys Pro His Gln
                565

<210> SEQ ID NO 2
<211> LENGTH: 450
<212> TYPE: PRT
<213> ORGANISM: Artificial Sequence
<220> FEATURE:
<223> OTHER INFORMATION: Protein translated from Synthetic DNA

<400> SEQUENCE: 2

Met Glu Ile Asp Glu Thr Leu Asp Val Lys Asn Thr Ser Arg Arg Met
1               5                   10                  15

Leu Val Gly Ala Gly Ala Val Gly Ser Leu Ala Ala Leu Ser Leu
                20                  25                  30

Gly Met Ser Pro Lys Ala Glu Ala Ala Lys Asp Ala Lys Ala Gly Pro
                35                  40                  45

Phe Asn Ser Pro Asn Thr Tyr Asp Val Thr Ala Trp Arg Ile Lys Gly
            50                  55                  60

Gln Pro Lys Val Thr Ala Glu Ser Asp Ile Gly Ala Val Ile Asn Asp
65                  70                  75                  80

Ile Ile Ala Asp Ile Lys Lys Arg Gln Thr Thr Pro Asp Thr Arg Pro
                    85                  90                  95

Gly Ala Val Val Ile Ile Pro Pro Gly Asp Tyr Asp Leu Arg Thr Gln
```

-continued

|   |   |   | 100 |   |   | 105 |   |   | 110 |   |   |
|---|---|---|---|---|---|---|---|---|---|---|---|
| Val | Val | Val | Asp | Val | Asp | Tyr | Leu | Thr | Ile | Ala | Gly | Phe | Gly | His | Gly |

Val Val Val Asp Val Asp Tyr Leu Thr Ile Ala Gly Phe Gly His Gly
            115                 120                 125

Phe Phe Ser Arg Ser Ile Lys Asp Asn Val Asp Pro Thr Gly Trp Leu
            130                 135                 140

Asn Leu Gln Pro Gly Gly Ser His Ile Arg Val Leu Thr Pro Pro Ser
145                 150                 155                 160

Ala Pro Gln Ala Phe Leu Val Arg Arg Ser Gly Ser Pro Arg Leu Ser
                165                 170                 175

Gly Ile Val Phe Arg Asp Phe Cys Leu Asp Gly Val Asn Phe Thr Pro
                180                 185                 190

Asp Gly Asn Ser Tyr Arg Asn Gly Lys Thr Gly Ile Glu Val Ala Ser
            195                 200                 205

Asp Asn Asp Ser Thr His Val Thr Gly Met Gly Phe Val Tyr Leu Glu
210                 215                 220

His Ala Leu Ile Val Arg Gly Ala Asp Ala Leu Arg Val His Asp Asn
225                 230                 235                 240

Met Ile Ala Glu Cys Gly Asn Cys Val Glu Leu Thr Gly Ala Gly Gln
                245                 250                 255

Ala Thr Ile Val Ser Gly Asn Leu Met Gly Ala Gly Pro Glu Gly Val
                260                 265                 270

Thr Leu Leu Ala Glu Asn His Glu Gly Leu Leu Val Thr Gly Asn Asn
            275                 280                 285

Phe Phe Pro Arg Gly Arg Ser Leu Ile Glu Phe Asn Gly Cys Asn Arg
        290                 295                 300

Cys Ser Val Ser Ser Asn Arg Phe Gln Gly Phe Tyr Pro Gly Met Met
305                 310                 315                 320

Arg Leu Leu Asn Gly Cys Lys Glu Asn Leu Ile Thr Ser Asn His Phe
                325                 330                 335

Arg Arg Gly Thr Glu Gly Phe Pro Pro Phe Ile Asn Arg Thr Asn Gly
            340                 345                 350

Leu Asp Asp Leu Tyr Gly Val Leu His Thr Leu Gly Asp Asn Asn Leu
            355                 360                 365

Ile Ser Asn Asn Leu Phe Ala Tyr Asp Val Pro Pro Asn Lys Gly Val
370                 375                 380

Pro Ala Gly Ala Gln Pro Thr Ile Ile Leu Ile Ala Gly Gly Asp Gly
385                 390                 395                 400

Asn Val Val Ala Thr Asn His Val Val Ser Asn Val Ala Thr Gln His
                405                 410                 415

Val Val Leu Asp Gly Ser Thr Thr His Ser Lys Val Leu Asp Ser Gly
            420                 425                 430

Ser Ala Thr Thr Ile Thr Ser Tyr Ser Pro Asp Thr Ala Ile Arg Pro
            435                 440                 445

Thr Pro
450